US008067241B2

(12) United States Patent
Gerdes et al.

(10) Patent No.: US 8,067,241 B2
(45) Date of Patent: Nov. 29, 2011

(54) METHOD AND APPARATUS FOR ANTIGEN RETRIEVAL PROCESS

(75) Inventors: Michael John Gerdes, Albany, NY (US); Anup Sood, Clifton Park, NY (US); Christopher James Sevinsky, Watervliet, NY (US)

(73) Assignee: General Electric Company, Niskayuna, NY (US)

( * ) Notice: Subject to any disclaimer, the term of this patent is extended or adjusted under 35 U.S.C. 154(b) by 196 days.

(21) Appl. No.: 12/547,768

(22) Filed: Aug. 26, 2009

(65) Prior Publication Data

US 2011/0053171 A1   Mar. 3, 2011

(51) Int. Cl.
*G01N 33/53* (2006.01)
(52) U.S. Cl. ............................ 436/86; 435/518
(58) Field of Classification Search .................. None
See application file for complete search history.

(56) References Cited

U.S. PATENT DOCUMENTS

| 2005/0032129 A1 | 2/2005 | Hasui |
| 2005/0053526 A1 | 3/2005 | Angros |
| 2007/0037138 A1 | 2/2007 | Winther |
| 2007/0154958 A1 | 7/2007 | Hamann et al. |
| 2008/0234204 A1* | 9/2008 | Smith et al. ............... 514/15 |

FOREIGN PATENT DOCUMENTS

| WO | WO0144784 A1 | 6/2001 |
| WO | WO2006007841 A2 | 1/2006 |
| WO | WO2009110936 A2 | 9/2009 |

OTHER PUBLICATIONS

Saito et al. J. Histochemistry 2003 vol. 51, p. 989-994.*
Kiernan et al. (Cutting Edge 2006 Review Article "Preservation and Retrieval of antigens for Immunohistochemistry", p. 5-11).*
Nirmalan et al., "Development and Validation of a Novel Protein Extraction Methodology for Quantitation of Protein Expression in Formalin-Fixed Paraffin-Embedded Tissues Using Western Blotting", Journal of Pathology, vol. 217, pp. 497-506, 2009.
Guo et al., Proteome Analysis of Microdissected Formalin-Fixed and Paraffin-Embedded Tissue Specimens, Journal of histochemistry & Cyatochemistry, vol. 55, No. 7, pp. 763-772, 2007.
Becker et al., "Quantitative Protein Analysis From Formalin-Fixed Tissues: Implications for Translational Clinical Research and Nanoscale Molecular Diagnosis", Journal of Pathology, vol. 211, pp. 370-378, 2007.
Shi et al., "Protein Extraction From Formalin-Fixed, Paraffin-Embedded Tissue Sections: Quality Evaluation by Mass Spectrometry", Journal of Histochemistry & Cytochemistry, vol. 54, vol. 6, pp. 739-743, 2006.
Bode et al., "Toponome Imaging System (TIS): Imaging the Proteome with Functional Resolution", Nature Methods, pp. iii-iv, Jan. 2007.
Farragher et al., "RNA Expression Analysis From Formalin Fixed Paraffin Embedded Tissues", Histochem Cell Biol, vol. 130, pp. 435-445, 2008.
Fischer et al., "Cryosectioning Tissues", Protocol, Cite as: Cold Spring Harb Protoc; doi:10.1101/pdb.prot4991, 9 pages, 2008.
Shi et al., "Antigen Retrieval Immunohistochemistry Under the Influence of pH Using Monoclonal Antibodies", Journal of Histochemistry & Cytochemistry, vol. 43, No. 2, pp. 193-201, 1995.
Boddy et al., "The Androgen Receptor is Significantly Associated With Vascular Endothelial Growth Factor and Hypoxia Sensing via Hypoxia-Inducible Factors HIF-1a, HIF-2a, and the Prolyl Hydroxylases in Human Prostate Cancer", Clinical Cancer Research, vol. 11, No. 21, pp. 7658-7663, Nov. 1, 2005.
Shi et al., "Antigen Retrieval Technique Utilizing Citrate Buffer or Urea Solution for Immunohistochemical Demonstration of Androgen Receptor in Formalin-Fixed Paraffin Sections", Journal of Histochemistry & Cytochemistry, vol. 41, No. 11, pp. 1599-1604, 1993.
Taylor et al., "Strategies for Improving the Immunohistochemical Staining of Various Intranuclear Prognostic Markers in Formalin-Paraffin Sections: Androgen Receptor, Estrogen Receptor, Progesterone Receptor, p53 Protein, Proliferating Cell Nuclear Antigen, and Ki-67 Antigen Revealed by Antigen Retrieval Techniques", Hum Pathol, vol. 25, No. 3, pp. 263-270, Mar. 1994.
Becker, et al., "Quantitative Protein Analysis from Formalin-fixed Tissues: Implications for Translational Clinical Research and Nanoscale Molecular Diagnosis", Journal of Pathology, 2007; 211: 370-378.
Niroshima et al., "Development and Validation of a Novel Protein Extraction Methodology for Quantitation of Protein Expression in Formal-fixed Paraffin-embedded Tissues Using Western Blotting", Journal of Pathology, 2009; 217: 497-506.
Fischer et al., "Cryosectioning Tissues", CSH Protocols, 2008, 1-2.
Guo et al., "Proteome Analysis of Microdissected Formalin-fixed and Paraffin-embedded Tissue Specimens", Journal of Histochemistry & Crtochemistry, vol. 55(7): 363-772, 2007.
Bode et al., "Toponome Imaging System (TIS): Imaging the Proteome with Functional Resolution", Jan. 2007, Topos Nomos Ltd., 3-4.
Shi et al., "Protein Extraction from Formalin-fixed, Paraffin-embedded Tissue Sections: Qia;otu Evaluation by Mass Spectrometry", Journal of >Histochemistry & Cytochemistry, vol. 54(6): 739-743, 2006.

(Continued)

*Primary Examiner* — Jacob Cheu
(74) *Attorney, Agent, or Firm* — Eileen W. Gallagher

(57) ABSTRACT

The invention provides a method for antigen retrieval of a formaldehyde-fixed tissue sample comprising incubating a formaldehyde-fixed tissue sample in a first antigen retrieval solution at a temperature of greater than 90° C., transferring the tissue sample to a second antigen retrieval solution, and incubating the tissue sample in the second antigen retrieval solution at a temperature of greater than 90° C. The invention also provides a kit and sample delivery device for carrying out the method.

12 Claims, 4 Drawing Sheets

OTHER PUBLICATIONS

Farragher et al.,, "RNA Expression Analysis from Formalin Fixed Paraffin Embedded Tissues", Histoc.hemistry and Cell Biology, vol. 130, No. 3, Sep. 2008, Abstract, 1-2.

U.S. Appl. No. 11/560,599, filed Nov. 16, 2006, entitled "Sequential Analysis of Biological Samples".

U.S. Appl. No. 11/864,098, filed Sep. 28, 2007, entitled "Sequential Analysis of Biological Samples".

U.S. Appl. No. 11/864,093, filed Sep. 28, 2007, entitled "Sequential Analysis of Biological Samples".

U.S. Appl. No. 11/864,085, filed Sep. 28, 2007, entitled "Sequential Analysis of Biological Samples".

Shi et al., "Antigen Retrieval Immunohistochemistry: Past, Present, and Future", Journal of Histochemistry & Cytochemistry, vol. 43, No. 3, pp. 327-343, 1997.

Yamashita et al., "Mechanisms of Heat-Induced Antigen Retrieval: Analyses In Vitro Employing SDS-PAGE and Immunohistochemistry", Journal of Histochemistry & Cytochemistry, vol. 53, No. 1, pp. 13-21, 2005.

D'Amico et al., "State of the Art in Antigen Retrieval for Immunohistochemistry", Journal of Histochemistry & Cytochemistry, vol. 341, pp. 1-18, 2009.

* cited by examiner

METHOD AND APPARATUS FOR ANTIGEN RETRIEVAL PROCESS

BACKGROUND

Diagnostic cell imaging uses methods whereby molecules produced by cells or tissues can be specifically localized to those cells or tissues. This provides a researcher with information as to the sites of production or activity of those given molecules. For the specific localization of proteins in routine pathology, a procedure known as immunohistochemistry (IHC) is routinely utilized. In IHC an antibody for a specific antigen is applied to a fixed tissue sample that recognizes a known specific molecule as a first step. This antibody is then detected with the use of a secondary antibody that has been chemically coupled with an enzyme, such as horseradish peroxidase. After incubation with a chromogenic substrate such as di-amino-benzidine (DAB), a colored deposit is produced at the site of the secondary antibody that has bound to the primary antibody at the specific site of the protein of interest. This procedure is currently utilized for over 200 antibodies in clinical pathology labs and many more in the research environment.

The nature of tissue processing requires that the samples be "fixed" prior to embedding in paraffin and micro-sectioning on a microtome to produce tissue sections suitable for immunostaining. During this process, proteins are preserved using a formaldehyde treatment that produces chemical cross-linking which preserves the cellular features of the tissue. Formaldehyde preserves or fixes tissue or cells predominantly by cross-linking primary amine groups in proteins with other nearby nitrogen atoms in protein or DNA through a —CH2— linkage. The process of tissue fixation however, frequently masks antigens on specific proteins for which detection is desirable for diagnostic and prognostic purposes. Typically procedures are optimized for detection of individual target molecules, and when needed, serial sections are processed in a different manner for the detection of additional targets molecules. With advances in the ability to detect multiple antigens in a single sample, there needs to be a uniform tissue processing that is compatible with the detection of multiple proteins.

BRIEF DESCRIPTION

In a first aspect, the invention provides a method of antigen retrieval of a formaldehyde-fixed tissue sample comprising the step of incubating the formaldehyde-fixed tissue sample in a first antigen retrieval solution at a temperature of greater than 90° C., transferring the tissue sample to a second antigen retrieval solution, and incubating the tissue sample in the second antigen retrieval solution at a temperature of greater than 90° C.

In a second aspect, the invention provides a kit for retrieving antigens in a formaldehyde-fixed tissue sample, comprising, a first antigen retrieval solution that retrieves at least a portion of unretrieved antigens in the sample, and a second antigen retrieval solution that retrieves at least some of another portion of unretrieved antigens in the sample.

In a third aspect, the invention provides a sample handling device for carrying out the an antigen retrieval method comprising a sample handling subsystem, a reagent dispensing subsystem, and a signal detection subsystem.

DRAWINGS

These and other features, aspects, and advantages of the present invention will become better understood when the following detailed description is read with reference to the accompanying drawings in which like characters represent like parts throughout the drawings.

DETAILED DESCRIPTION

Figure 1:
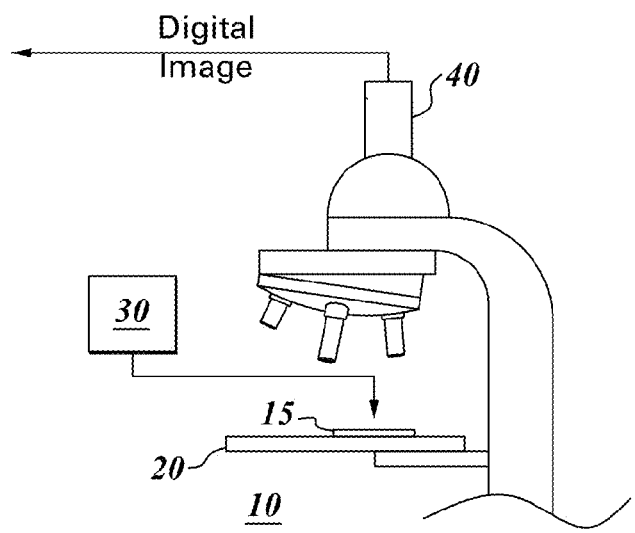
FIG. 1 is a representative sample handling device for contacting a formaldehyde fixed tissue sample with an antigen retrieval solutions.

To more clearly and concisely describe and point out the subject matter of the claimed invention, the following definitions are provided for specific terms that are used in the following description and the claims appended hereto.

Definitions

"Antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')$_2$, or Fab'). In addition, aggregates, polymers, and conjugates of immunoglobulins or their fragments may be used where appropriate so long as binding affinity for a particular molecule is substantially maintained.

"Antigen" refers to a substance that may bind an antibody or antibody fragment. Antigens may be endogenous whereby they are generated within the cell as a result of normal or abnormal cell metabolism, or because of viral or intracellular bacterial infections. Endogenous antigens include xenogenic (heterologous), autologous and idiotypic or allogenic (homologous) antigens. Antigens may also be tumor-specific antigens or presented by tumor cells. In this case, they are called tumor-specific antigens (TSAs) and, in general, result from a tumor-specific mutation. Antigens may also be tumor-associated antigens (TAAs), which are presented by tumor cells and normal cells. Antigen also includes CD antigens, which refers any of a number of cell-surface markers expressed by leukocytes and can be used to distinguish cell lineages or developmental stages. Such markers can be identified by specific monoclonal antibodies and are numbered by their cluster of differentiation.

"FISH" and "CISH" refer to fluorescent in situ hybridization and chromagenic in situ hybridization respectfully. FISH is a cytogenetic technique used to detect and localize the presence or absence of specific DNA sequences on chromosomes or RNA sequences at transcription sites as well as in other parts of the cell. FISH uses fluorescent probes that bind to only those parts of the chromosome with which they show a high degree of sequence similarity. CISH allows detection of gene amplification, chromosome translocations and chromosome number using conventional enzymatic reactions under the brightfield microscope on formalin-fixed, paraffin-embedded (FFPE) tissues.

"Immunostaining" refers to an anitbody-based method to detect a specific protein in a sample. Immunostainging includes both immunocytochemical staining and immunhistochemical staining. Immunocyctochemical (ICC) staining refers to a techniue that uses antibodies which target antigenson the cells. This may be performed to determine the presence of certain diseases, for example, types of cancer. Immunohistochemical (IHC) staining refers to the staining and localization of antigens in tissue sections by the use of labeled antibodies as specific reagents through antigen-antibody interactions that are visualized by a marker such as fluorophores, reacted enzyme substrates, radioactive element or colloidal gold.

"Probe" refers to an agent having a binder and a label, such as a signal generator or an enzyme. In some embodiments, the binder and the label (signal generator or the enzyme) are embodied in a single entity. As used herein "binder" refers to a molecule capable of reacting with or associating with another molecule, such as an antigen binding to an antibody. The binder and the label may be attached directly (e.g., via a fluorescent molecule incorporated into the binder) or indirectly (e.g., through a linker, which may include a cleavage site) and applied to the tissue sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a tissue sample in a single step or multiple steps. The term "fluorescent probe" refers to an agent having a binder coupled to a fluorescent signal generator.

"Signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators include one or more of a chromophore, a fluorophore, a Raman-active tag, or a radioactive label. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

"Fluorophore" or "Fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515 to 540 nanometers. Red fluorophores (for example Texas Red, Cy5, and tetramethylrhodamine) may be characterized by their emission at wavelengths generally in the range of 590 to 690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl] naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

"Target" refers to the component of a tissue sample that may be detected when present in the tissue sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids. In some embodiments, targets may include both proteins and nucleic acids.

The invention includes embodiments that relate generally to methods applicable in analytical, diagnostic, or prognostic applications such as analyte detection, histochemistry, immunostaining, immunohistochemistry, immunocytochemistry or immunofluorescence. In some embodiments, the methods disclosed herein may be particularly applicable in immunohistochemistry and immunocytochemistry.

In accordance with one embodiment, a method is described in which a tissue section derived from pathological sampling is processed prior to protein detection for biomarker assessment. In one embodiment, the method comprises a two-step procedure that is applicable to multiple protein antigens and may provide for high level of antigen retrieval. In certain embodiments, this allows for multiplexing diagnosis of clinically relevant samples.

In some embodiments, a tissue sample includes tissue sections from healthy or diseased tissues (e.g., tissue sections from colon, breast tissue, prostate). A tissue sample may include a single part or piece of a tissue section, for example, a thin slice of tissue or cells cut from a tissue section. In some embodiments, the same section of tissue sample may be analyzed at both morphological and molecular levels.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuecan. Once the tissue sample is embedded, the sample may be sectioned by a microtome into sections. The thickness of the sections may vary based on the type of tissue and analysis. In certain embodiments the sections may have a preferred thickness in a range of from about two microns to about five microns.

Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In other embodiments, the formaldehyde fixed tissue sample may be adhered to a solid support in order to allow for its analysis, transfer and movement during the preparation and imaging processes. The tissue sample may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

In one embodiment a method is described in which a formaldehyde fixed tissue sample is contacted with a first antigen retrieval solution and heated to a temperature of greater than 90° C. for a period of greater than 10 minutes, more preferable for a period of approximately 20 minutes. Heating may occur using a pressure cooker, autoclave, water bath, hot plate, microwave, or steam heater, to provide uniform heating to the tissue sample immersed in the antigen retrieval solution. The tissue sample is then transferred without additional treatment to a second antigen retrieval solution that was pre-heated to a temperature of greater than 90° C., for a similar period of time. Pre-heating may occur using a pressure cooker, autoclave, water bath, hot plate, microwave, steam heat or a combination thereof and can be performed at the time of heating the first antigen retrieval solution. Preferably the incubation of the sample in the second antigen retrieval solution occurs at atmospheric pressure, and by immersion only in the hot solution. This may prevent tissue damage.

In one embodiment, the first antigen retrieval solution is a buffer solution having a pH range between about 5 and about 7. The first antigen retrieval solution may be a commonly used buffer solution used to maintain pH in the range of slightly acidic to neutral. In certain embodiments the buffer may comprise citric acid, potassium dihydrogen phosphate, boric acid, diethyl barbituric acid, piperazine-N,N'-bis(2-ethanesulfonic acid), dimethylarsinic acid, 2-(N-morpholino)ethanesulfonic acid, or a combinations thereof. In other embodiments, the buffer solution may be a citric acid sodium phosphate buffer solution having a pH of approximately 6.0 at elevated temperatures.

With the application of heat, the first antigen retrieval solution may act to hydrolyze crosslink bonds, which may have formed between the formalin and antigen, during sample fixation. This results in at least some portion of the antigen in the sample being retrieved.

In one embodiment, the second antigen retrieval solution is a buffer solution having an alkaline pH in the range of about 7.5 to about 11. The second antigen retrieval solution may be a commonly used buffer solution use to maintain pH in a slightly alkaline range. In certain embodiments, the buffer solution may be comprised of tris(hydroxymethyl)methylamine (TRIS), 2-(N-morpholino)ethanesulfonic acid (TAPS), N,N-bis(2-hydroxyethyl)glycine(Bicine), N-tris(hydroxymethyl)methylglycine (Tricine), 4-2-hydroxyethyl-1-piperazineethanesulfonic acid (HEPES), 2-{[tris(hydroxymethyl)methyl]amino}ethanesulfonic acid (TES), or a combination thereof. In another embodiment, the buffer solution may be a TRIS-HCl buffer having a pH of approximately 10 at elevated temperatures.

As with the first antigen retrieval solution, the second antigen retrieval solution may act to hydrolyze crosslink bonds, which may have formed between the fomalin and antigen during sample fixation. The portion of the antigen being retrieved is at least some of another portion of unretrieved antigens in the sample.

It should be appreciated that in other embodiments, the first antigen retrieval solution may be a buffer solution in the range of about 7.5 to about 11 and the second antigen retrieval solution may be a buffer solution in the range of about 5 to about 7.

The antigen retrieved by exposure to the first and second antigen retrieval solutions may be more susceptible to immunostaining to allow for both analytical and functional morphology studies. Immunostaining includes both immunohistochemical (IHC) staining and immunocytochemical (ICC) staining. In certain embodiments improvement may include increased intensity of positive staining and decrease background staining.

In certain embodiments, after the application of the second antigen retrieval solution, immunostaining of the sample may occur. An antibody solution (e.g. a probe) may be contacted with the tissue section for a sufficient period of time and under conditions suitable for binding of the labeled-antibody to the antigen. Two detection methods may be used: direct or indirect. In a direct detection, a signal generator-labeled primary antibody (e.g., fluorophore-labeled primary antibody) may be incubated with an antigen in the tissue sample, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In embodiments where the secondary antibody may be conjugated to an enzymatic label, a chromogenic or fluorogenic substrate may be added to provide visualization of the antigen. In some embodiments two or more (at most four) primary antibodies (labeled or unlabeled) may be contacted with the tissue sample. Unlabeled antibodies may be then contacted with the corresponding labeled secondary antibodies. In some embodiments, other methods may be employed for signal enhancement such as the use of a labeled tertiary or quaternary antibody.

In some embodiments after the antigen retrieval process, nucleic acid probes are applied to the sample to perform fluorescent in situ hybridization (FISH) or chromagenic in situ hybridization (CISH).

A signal from the signal generator in the probe may be detected using a detection system. The nature of the detection system used may depend upon the nature of the signal generators used. The detection system may include an electron spin resonance (ESR) detection system, a charge coupled device (CCD) detection system (e.g., for radioisotopes), a fluorescent detection system, an electrical detection system, a photographic film detection system, a chemiluminescent detection system, an enzyme detection system, an atomic force microscopy (AFM) detection system and a scanning tunneling microscopy (STM) detection system (both used for example in the detection of microbeads), an optical detection system, a near field detection system, or a total internal reflection (TIR) detection system.

One or more of the aforementioned techniques may be used to observe one or more characteristics of a first signal from a first signal generator. In some embodiments, signal intensity, signal wavelength, signal location, signal frequency, or signal shift may be determined using one or more of the aforementioned techniques. In some embodiments, one or more aforementioned characteristics of the signal may be observed, measured, and recorded. In some embodiments, a signal generator may include a fluorophore and fluorescence wavelength or fluorescent intensity may be determined using a fluorescence detection system. In some embodiments, a signal may be observed in situ, that is, a signal may be observed directly from the signal generator associated through the binder to the target in the tissue sample. In some embodiments, a signal from the signal generator may be analyzed within the tissue sample, obviating the need for separate array-based detection systems. In other embodiments, after probe binding, the signal may be separated from the binder and detected away from the biological sample. Methods for the separation of the signal may include, but is not limited to ELISA and mass spectrometry, hybridization microarrays.

In some embodiments, observing a signal may include capturing an image of the tissue sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitized image). The same procedure may be repeated for different signal generators (if present) that are bound in the sample using the appropriate fluorescence filters.

A chemical agent may be applied to the tissue sample to modify the signal. In some embodiments, signal modification may include one or more of a change in signal characteristic, for example, a decrease in intensity of signal, a shift in the signal peak, a change in the resonant frequency, or cleavage (removal) of the signal generator resulting in signal removal.

In some embodiments, a chemical agent may be in the form of a solution and the tissue sample may be contacted with the chemical agent solution for a predetermined amount of time. The concentration of the chemical agent solution and the contact time may be dependent on the type of signal modification desired. In some embodiments, the contacting conditions for the chemical agent may be selected such that the binder, the target, the tissue sample, and binding between the binder and the target may not be affected. In some embodiments, a chemical agent may only affect the signal generator and the chemical agent may not affect the target/binder binding or the binder integrity. Thus by way of example, a binder may include a primary antibody or a primary antibody/secondary combination. A chemical agent according to the methods disclosed herein may only affect the signal generator, and the primary antibody or primary antibody/secondary antibody combination may essentially remain unaffected. In some embodiments, a binder (such as, a primary antibody or primary antibody/secondary antibody combination) may remain bound to the target in the tissue sample after contacting the sample with the chemical agent. In some embodiments, a binder may remain bound to the target in the tissue sample after contacting the sample with the chemical agent and the binder integrity may remain essentially unaffected (for example, an antibody may not substantially denature or elute in the presence of a chemical agent). In other embodiments, the chemical agent may affect target/binder binding or binder/signal contacts/linkages.

In some embodiments, multiple targets may be detected through "stripping of the probe and reprobing the sample. Stripping generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of the probe from the sample. In some embodiments, multiple targets may be detected through the use of light to fluorescently bleach the reporter or signal generator, thereby allowing that signal generator to be re-used on a new probe. These processes may be repeated re-iteratively to achieve multiple probings of the same sample.

In some embodiments, a characteristic of the signal may be observed after contacting the sample with a chemical agent to determine the effectiveness of the signal modification. For example, a color may be observed before application of the chemical agent and the color may be absent after application of the chemical agent. In another example, fluorescence intensity from a fluorescent signal generator may be observed before contacting with the chemical agent and after contacting with the chemical agent. In some embodiments, a decrease in signal intensity by a predetermined amount may be referred to as signal modification. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in the signal intensity by an amount in a range of greater than about 80 percent.

In some embodiments, the tissue sample may be contacted with a second probe using one or more procedures described herein above for the first probe. The second probe may be capable of binding to target different from the target bound by the first probe. In embodiments where a plurality of probes may be contacted with the tissue sample in the first probe contact step, the second probe may be capable of binding a target different from the targets bound by the first probe set. In some embodiments, a tissue sample may be contacted with a plurality of probes in the second probe contact step.

One or more detection methods described hereinabove may be used to observe one or more characteristics of a subsequent (e.g., second, third, etc.) signal from a second signal generator (present in the subsequent probe). In some embodiments, signal intensity, signal wavelength, signal location, signal frequency, or signal shift may be determined using one or more of the aforementioned techniques. Similar to the first signal, a subsequent signal (for example, a fluorescence signal) obtained may be recorded in the form of a digital signal (for example, a digitized image). In some embodiments, observing a subsequent signal may also include capturing an optical image of the tissue sample.

In some embodiments, after contacting the sample with a subsequent (e.g., second, third, etc.) probe, agent modification and subsequent probe administration may be repeated multiple times. In some embodiments, after observing a second signal from the second probe, the tissue sample may be contacted with a chemical agent to modify the signal from the second probe. Furthermore, a third probe may be contacted with the tissue sample, wherein the third probe may be capable of binding a target different from the first and the second probes. Likewise, a signal from the third probe may be observed followed by application of chemical agent to modify the signal. The contacting, binding, and observing steps may be repeated iteratively multiple times using an nth probe capable of binding to additional targets to provide the user with information about a variety of targets using a variety of probes and/or signal generators.

In some embodiments, a series of probes may be contacted with the tissue sample in a sequential manner to obtained a multiplexed analysis of the tissue sample. In some embodiments, a series of probe sets (including about 4 probes in one set) may be contacted with the tissue sample in a sequential manner to obtain a multiplexed analysis of the tissue sample. Multiplexed analysis generally refers to analysis of multiple targets in a tissue sample using the same detection mechanism.

In certain embodiments a kit useful for carrying out the methods of antigen retrieval described above is provided. The kit may comprise one or more of the antigen retrieval solutions. The kit may also further comprise instruction for use.

In some embodiments, a kit will include one or more additional reagent for immunostaining and detection. For example, in some embodiments, the kit may include a signal generator such as a chromophore, a fluorophore, a Raman-active tag, or a radioactive label. The kit may also include reagents, which may improve detection or amplify the signal as described above including, but not limited to, polymerase enzyme, other buffers, metal cations and salts.

In accordance with one embodiment, as shown in FIG. 1 a sample handling device 10 is described for contacting a formaldehyde fixed tissue sample 15 with the aforementioned antigen retrieval and other washing and staining solutions. The sample handling device may be comprised of a sample handling subsystem 20 and a reagent dispensing subsystem 30. In certain embodiments, the device may also include a signal detection subsystem 40. In one of the embodiments, the sample handling device may be incorporated as a component of an analytical device such as an automated high-throughput system that is capable of staining and imaging formaldehyde-fixed tissue sample in one system and still further analyzes the images.

As such, in one embodiment, the system may include a sample handling subsystem for positioning and moving the formaldehyde-fixed tissue sample for analysis and a reagent dispensing subsystem to contact the sample with at least one of a first antigen retrieval solution, a second antigen retrieval solution, and an immunostaining reagent. The sample handling system may involve multiple components and allow movement of the sample from one area to the next. For example, the sample may be contacted with reagents using one device, and moved and affixed to a stage for imaging, the movement of the stage being controllable. The stage may be incorporated into a microscope and capable of moving the sample through an imaging field.

The system may also include a signal detection subsystem (not shown) to capture images of the sample through the staining process. The image may be captured using various illumination sources. In certain embodiments, the image capture may be part of an imaging microscope capable of capturing and transferring a digital image of the sample at various magnifications. In still another embodiment the automated system may include a computer-readable medium that may includes instructions for the automated technique for the analysis of the stained formaldehyde-fixed tissue sample.

In other embodiments, the sample handling device may be capable of cycling through multiple steps of antigen retrieval, fluorescence tagging, imaging, and stripping of the fluorescent probe. Staining may also involve immunoperoxidase labeling. In one embodiment an alcohol-soluble peroxidase substrate, 3-amino-9-ethylcarbazole (AEC), may be used followed by removal of the AEC precipitate, optional further inactivation of the peroxidase with a mild peroxide treatment and repeated staining. In other embodiments, the fluorescent probe may be stripped through a chemical treatment, a heat treatment or a combination there of.

The sampling handling device may be automated such that the multiple cycles may occur in situ, to minimize displacement of the sample and to aid in mapping of multiple markers in one tissue sector or cell sample.

EXPERIMENTAL

Methods

Variables that affect the signal to noise ration, which is a reflection of the sensitivity of the system, were analyzed using a design of experiment (DOE) approach. Variables included temperature, exposure time, pH, and washing sequence. Images were acquired using a Zeiss Axilmager Z1 microscope at 20× or 63× magnification. Quantification of the images was done using GNU Image Manipulation Program (GIMP) software calculating average pixel intensity per area after subtracting background pixel intensity from non-stained areas. Average pixel intensity was calculated as the average of 10 images of the same tissue.

The following materials were used for the study: human archival tissue was from a variety of sources and included samples for breast, prostate, lung, colon, placenta, salivary gland, lymph node, brain, and skin. All samples were from tissue archives. The specifics for fixation used are unknown and are presumed to have followed standard pathology practice. Antibodies for AR were obtained from Lab Vision Corporation (part of Thermo Fisher Scientific) and were conjugated in house with Cy3 and Cy5 fluorochromes using standard procedures. Citrate based antigen retrieval solution was obtained from Vector Laboratories and diluted 1:20 with a final pH value of 6.0. A Tris based buffer consisted of 10 mM Tris (tris(hydroxymethyl)aminomethane), 1 mM EDTA (ethylenediaminetetraacetic acid), 1% Tween-20 (polyoxyethylenesorbitan monolaureate) to give a pH value of 8 (made from a freshly prepared 10× stock solution). A standard home pressure cooker was used for heating, set on HI power, for 20 minutes and manually monitored.

Formalin fixed paraffin embedded tissue sections were processed by baking the slides at 65° C. for 1 hour and removing the wax from the sample section with a histochoice clearing agent. It was found that baking the samples was not required, but was used through out as a standard practice.

The samples were then processed through a series of alcohol washes of decreasing concentration (100, 95, 70, 50% typically), each for 2× 10 minute washes, and then brought to saline conditions in PBS solution for 10 minutes. The samples were then premeablized with a brief treatment in PBS containing 0.3% Triton X-100 followed by a retrieval process.

The retrieval process included placing the samples into a Solution A (Tris pH 8.0 with 1% Tween 20) in a pressure cooker or microwave for approximately 20 minutes. At the end of the heat cycle, the samples were placed into a preheated solution B (citrate solution pH 6) in a heated chamber without additional heat. The samples were not transferred to a cold PBS solution in between the two hot solutions, nor exposed to additional heat in the second solution. After the samples in the second solution had come to room temperature (approximately 20 minutes), the samples were rinsed in PBS extensively prior to any additional processing step such as blocking or peroxidase treatment (for endogenous peroxidase inactivation).

The samples may then undergo immuno-detection. After a first round of immuno-detection detection, samples may be cleared of signal and re-probed for additional antigens.

Alternatively, slides were processed using a Discovery® XT Autostainer (Ventana Medical Systems, Inc.). using a program setting similar to the manual process conditions. After bar-coding samples and preparing reagents, slides are loaded in to the autostainer and processed as follows: samples were heated and dewaxed by rinsing in an EZ-prep reagent (wax removal solution for Ventana Discovery XT). Antigen retrieval was performed using CC1 and CC2 (two solutions for antigen retrieval supplied by Ventana for use on the Discovery XT autostainer), Tris and Citric acid based solutions, respectively. For the purpose of comparison to the manual two-step method, short and intermediate time antigen retrievals were conducted which were referenced as mild and standard in the Discovery XT Autostainer program. It should be noted that on automated systems, tissue samples are rinsed between the two antigen retrieval steps, a key difference between the manual process described here and the automated processes. Slides were then stained manually along side samples processed by the two-step manual method.

Results and Observations

The use of an androgen receptor antibody for detection of AR in human archival prostate tissue sections was initially selected for analysis. This combination was chosen due to the lack of detectable signal produced when staining is done in the absence of epitope unmasking (not shown). Using two common buffers for antigen unmasking, citrate or Tris, and treating the samples for 20 minutes in a pressure cooker staining of moderate intensity was produced using a fluorescent dye. The citrate unmasking conditions that were used represents commonly used protocol for detection of AR by a variety of antibodies. Various conditions were tested including Citrate alone (set 1), Tris alone (set 2), Tris then Citrate (set 3), and Citrate then Tris (set 4). All conditions were tested on slides in triplicate, except the control samples where ten slides were stained to establish a baseline measurement.

Figure 2:
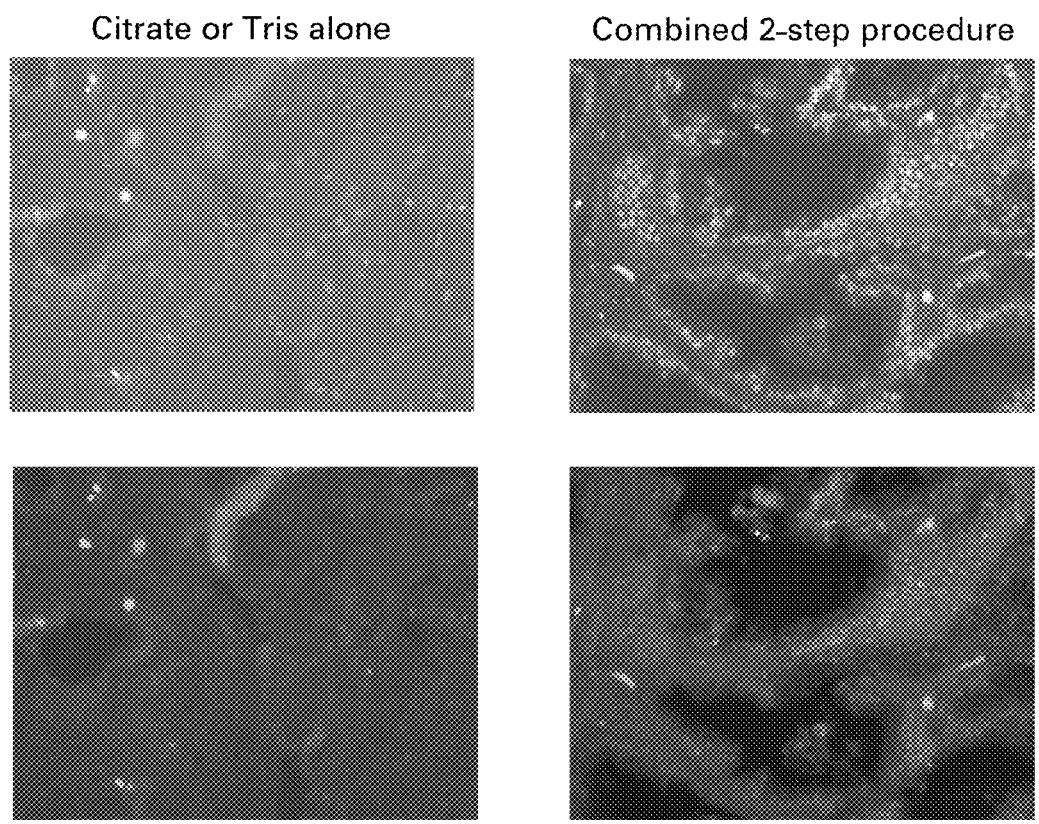
FIG. 2 is a monochromatic micrograph (at 20× or 63× magnification) showing enhanced staining using a two-step procedure compared to a one step procedure.

A first series of experiments used the Lab Vision AR antibody followed by detection with donkey anti-rabbit Cy3 secondary antibody. All data acquisition used equal exposure times and images were collected immediately after staining. As shown in FIG. 2, the two-step process provided a significant enhancement to staining for AR when compared to either citrate or tris alone. FIG. 2 is a monochromatic image of the staining showing enhanced staining on the right using a two step procedure.

In general, for each set of slides, a two fold or more increase in staining intensity was observed for AR with a two-step method compared to a control sample. Time of exposure to a heated solution was controlled with all slides receiving a total time of 50 minutes. The first heated step was done under pressure in a household pressure cooker for all the experimental slides. After 25 minutes, slides from sets 1 and 2 were put into a new jar of preheated solution (same solution as in the first step heated in separate jars while the first step is underway) and allowed to cool in the pressure cooker (not under pressure) for an additional 25 minutes. Slides were then washed in PBS and stained overnight at 4° C. with the primary antibody. For slides from sets 3 and 4, the solutions were changed to the respective conditions, as described above, during the latter 25 minutes of treatment and processed in parallel with the other sets.

Several permutations on the two-step procedure were also tested. In one permutation, the sequence in which the two solutions were used did not influence the results. No differences in results were observed if the acidic solution was used first, followed by the basic, or vice versa.

Other permutations in the method proved to be detrimental to the process. These included re-pressurizing the sample for the second heating period, and washing in PBS in between the first and second steps. Both of these changes resulted in a dramatic loss of tissue from the slide and were thus avoided.

After testing on primary antibodies to AR and detection with secondary antibodies, Cy5-directly conjugated AR antibodies were tested. Similar results were found using the direct conjugates whereby enhanced staining was observed in testing of a wide sampling of other commercially available antibodies. The process has also resulted in enhanced staining using a number of commercial grade phospho-epitopes, which are often unstable and prone to degradation in retrieval processes.

This procedure may also be applied for other applications such as protein isolation from FFPE tissues where antigen retrieval methods have been shown to enhance protein extraction and recovery. The procedure may also have use in laser capture micro dissection from FFPE tissues as a source of proteins for proteomic analysis.

Figure 3:
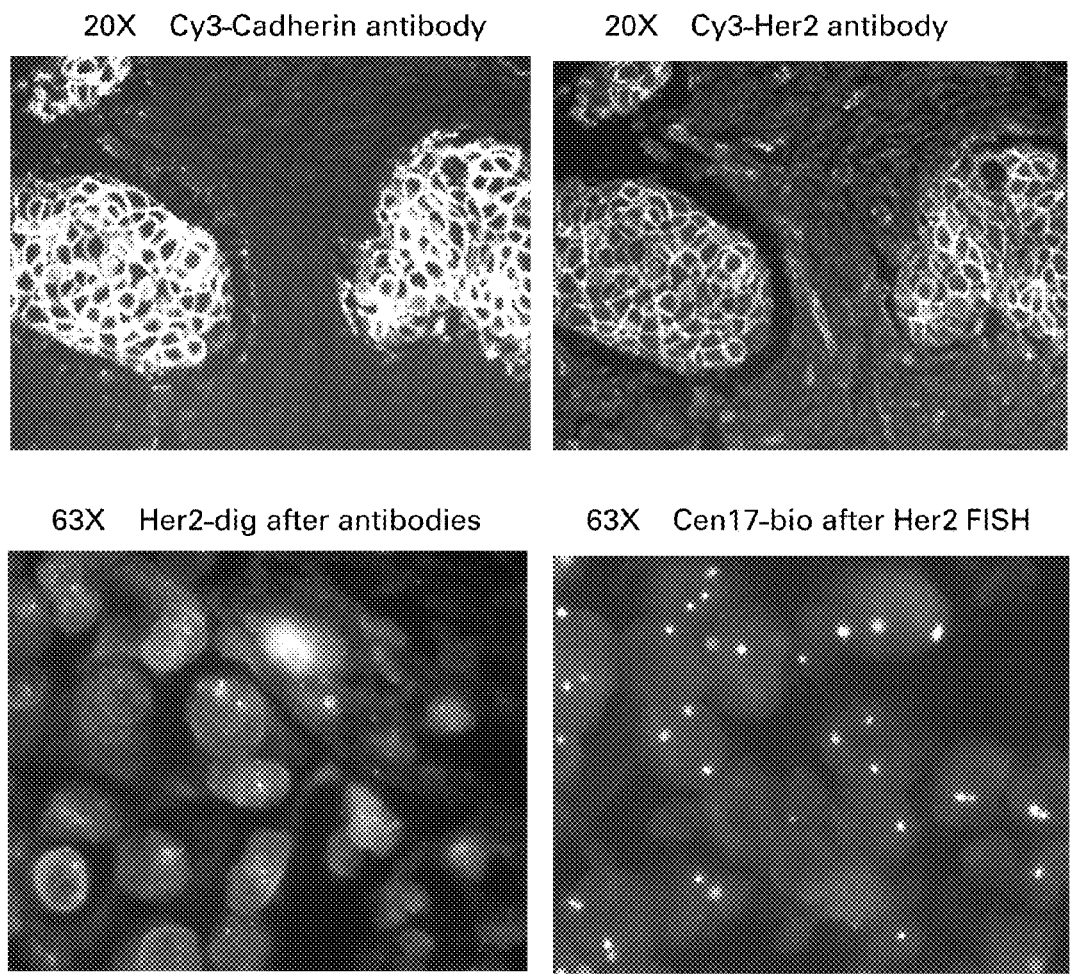
FIG. 3 shows monochromatic micrographs (at 20× magnification) showing enhanced staining using a two step procedure in a multiplex analysis FISH of BrCA tumor.

In another embodiment, the invention may be used on FFPE samples prior to FISH or CISH analysis. Typically, FFPE sample undergoing FISH or CISH analysis will be exposed to a heat pre-treatment step prior to DNA denaturation and probe hybridization. In accordance with one embodiment the two-step procedure may be substituted for the heat pre-treatment step or other procedures used to prepare the tissue sample prior to FISH or CISH analysis. FIG. 3 shows monochromatic micrographs (at 20× and 63× magnification) showing enhanced staining using a two step procedure in a multiplex FISH analysis of BrCA tumor using various antibodies.

Method Comparison

An automated process was also evaluated using the Discovery XT Autostainer. There were differences in process conditions between the autostainer and the manual two-step process related to the operation of the instrument. For instance, the autostainer used heat and detergent to dewax samples, while the manual process used the non-toxic Histochoice™ wax clearing reagent (Amresco).

Formalin-fixed, paraffin-embedded (FFPE) LNCaP cells (American Type Culture Collection (ATCC, Maryland) were stained for S6, phospho-S6 ser235/236, or phospho-S6 ser240/244 after the cells were prepared by manual two-step antigen retrieval described here, or by two similar methods using the Discovery XT autostainer. While antigen retrieval was accomplished using a manual or automated process, differences were observed in sequential signal removal/modification and restaining. In most cases a reduction in staining results from 1 or 5 signal modification steps using the automated system. For S6 a complete loss of staining resulted after just one round of signal modification using the automated methods. In all cases manual two step method providing the best preservation of each antigen. The manual two step method also showed less sensitivity when staining either phospho-epitope.

Figure 4:
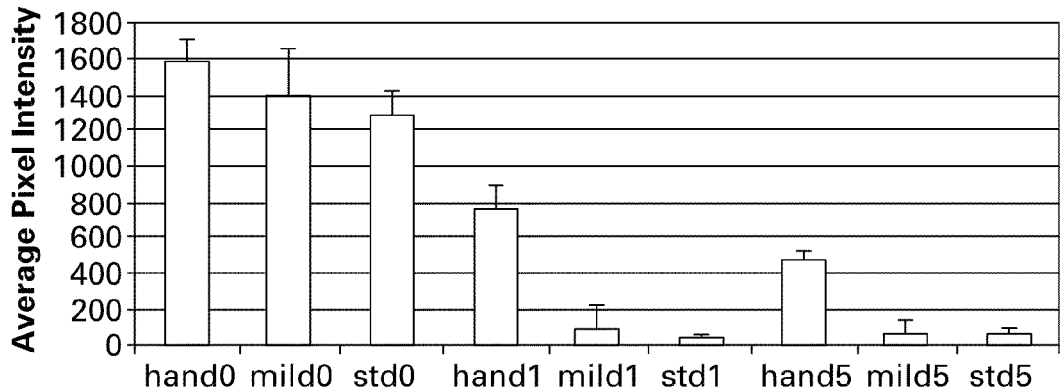
FIG. 4 is a bar chart of quantitative analysis results comparing a manual two-step antigen retrieval method to automated methods.
Figure 4:
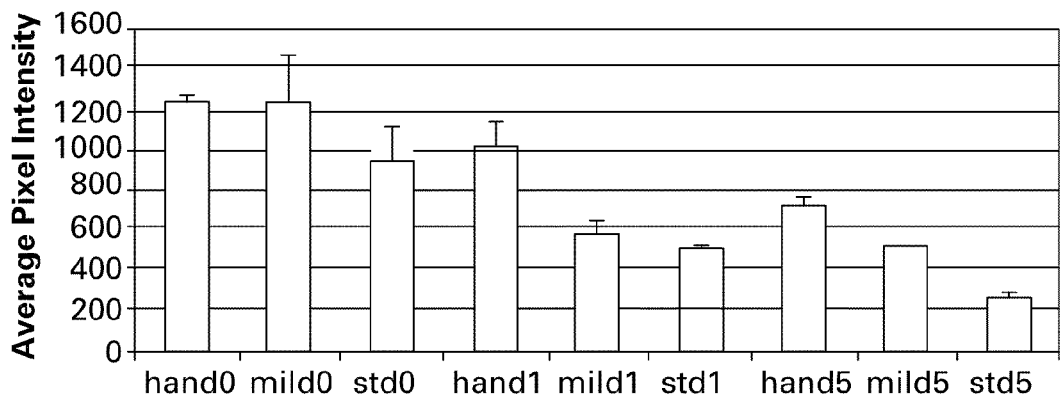
Figure 4:
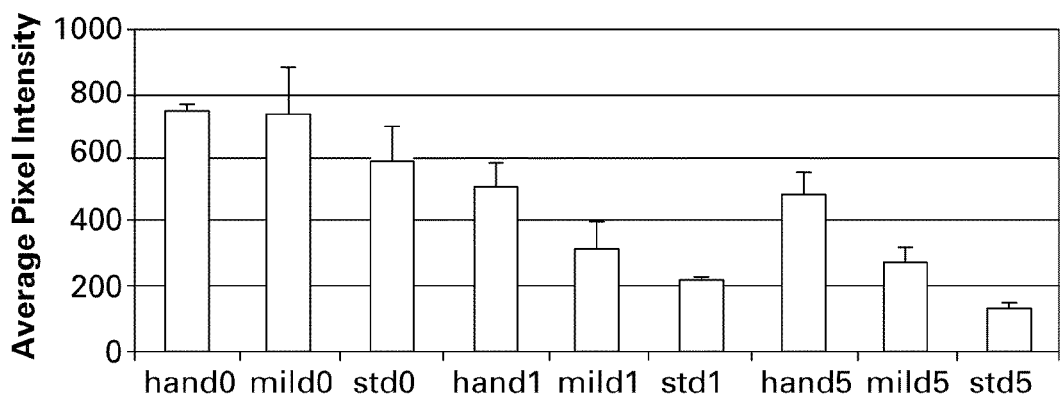
Figure 5:
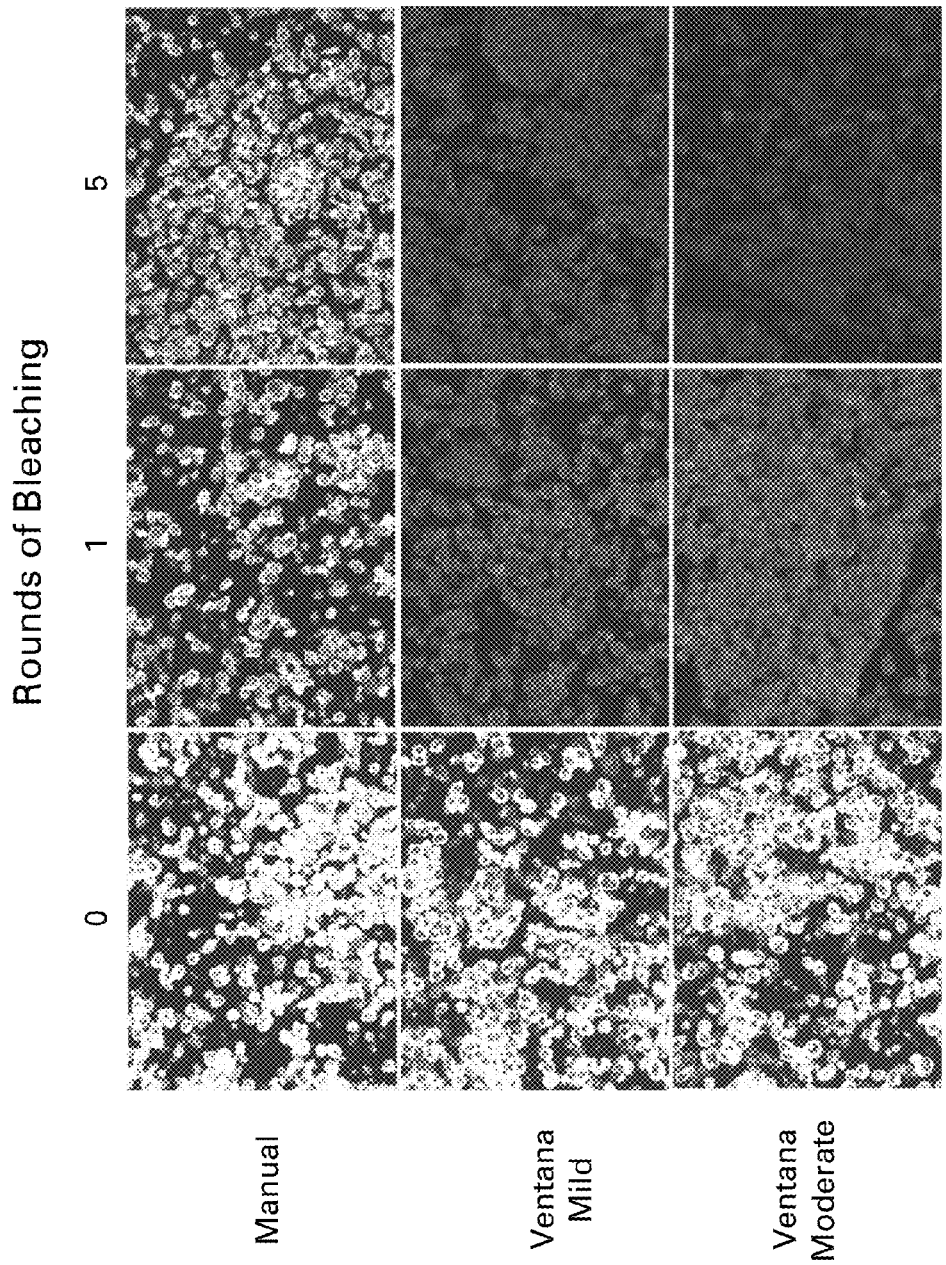
FIG. 5 shows monochromatic micrographs (at 20× magnification) of the bleaching effect on antigen-S6 staining on sample prepared by either the manual two-step antigen retrieval method or one of two automated antigen retrieval processes.

The differences are illustrated in FIG. 4, which is a graphic representation of a quantitative analysis comparing the greater epitope stability provided by the manual two-step antigen retrieval method compared to two automated processes. The average pixel intensities are shown evaluating the bleaching effect on antigen-S6. Slides were prepared by three different dewaxing and antigen retrieval methods and subjected to 0, 1, and 5 rounds of bleaching before being stained. Quantitative analysis indicated the manual two-step method best preserved the antigen. Different epitopes on the same protein responded differentially to bleaching, which may indicate a predominantly epitope effect, not loss of protein. This is also shown in FIG. 5, which are monochromatic micrographs (at 20× magnification) of the bleaching effect on antigen-S6 comparing the manual two-step antigen retrieval method to two automated processes.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of antigen retrieval of a formaldehyde-fixed tissue sample comprising the steps of:
    incubating the formaldehyde-fixed tissue sample in a first antigen retrieval solution at a temperature of greater than 90° C.;
    transferring the formaldehyde-fixed tissue sample to a second antigen retrieval solution;
    incubating the formaldehyde-fixed tissue sample in the second antigen retrieval solution at a temperature of greater than 90° C.; and
    wherein the first antigen retrieval solution comprises a buffer solution having a pH range of between about 5 and about 7 and the second antigen retrieval solution comprises a buffer solution having a pH range of between about 7.5 and about 11; or
    the first antigen retrieval solution comprises a buffer solution having a pH range of between about 7.5 and about 11 and the second antigen retrieval solution comprises a buffer solution having a pH range of between about 5 and about 7.

2. The method of claim 1 wherein the buffer solution having a pH range between about 5 and about 7 comprises citric acid, potassium dihydrogen phosphate, boric acid, diethyl barbituric acid, piperazine-N,N'-bis(2-ethanesulfonic acid), dimethylarsinic acid, 2-(N-morpholino)ethanesulfonic acid, or a combination thereof.

3. The method of claim 2, wherein the buffer solution having a pH range of between about 5 and about 7 comprises citric acid.

4. The method of claim 1, wherein the buffer solution having a pH range of between about 7.5 and about 11 comprises tris(hydroxymethyl)methylamine (TRIS), 2-(N-morpholino)ethanesulfonic acid (TAPS), N,N-bis(2-hydroxyethyl)glycine(Bicine), N-tris(hydroxymethyl)methylglycine (Tricine), 4-2-hydroxyethyl-1-piperazineethanesulfonic acid (HEPES), 2-{[tris(hydroxymethyl)methyl]amino }ethanesulfonic acid (TES), or a combination thereof.

5. The method of claim 4, wherein the buffer solution having a pH range of between about 7.5 and about 11 comprises TRIS.

6. The method of claim 1, wherein the formaldehyde-fixed tissue sample is embedded in paraffin.

7. The method of claim 1, wherein the formaldehyde-fixed tissue sample is a sectional portion of an organ or tissue, body fluid, a tissue or microarray.

8. The method of claim 1, wherein the incubating steps with the first antigen retrieval solution and the second antigen retrieval solution comprises incubation in a heating device for a period of greater than ten minutes.

9. The method of claim 8 wherein the heating device is a pressure cooker, autoclaving, water bath, hot plate, microwave, steam heating, or combination thereof.

10. The method of claim 1 further comprising the step of immunostaining of antigens.

11. The method of claim 10 wherein the immunostaining comprises sequential immunoperoxidase labeling and erasing.

12. The method of claim 1 wherein the formaldehyde-fixed tissue sample undergoes fluorescent in situ hybridization (FISH) or chromagenic in situ hybridization (CISH) analysis.

* * * * *

UNITED STATES PATENT AND TRADEMARK OFFICE
CERTIFICATE OF CORRECTION

| | | |
|---|---|---|
| PATENT NO. | : 8,067,241 B2 | Page 1 of 1 |
| APPLICATION NO. | : 12/547768 | |
| DATED | : November 29, 2011 | |
| INVENTOR(S) | : Gerdes et al. | |

It is certified that error appears in the above-identified patent and that said Letters Patent is hereby corrected as shown below:

In Column 6, Line 28, delete "TRIS-HCI" and insert -- TRIS-HCl --, therefor.

In Column 14, Line 31, in Claim 6, delete "paraffm." and insert -- paraffin. --, therefor.

Signed and Sealed this
Thirty-first Day of January, 2012

David J. Kappos
*Director of the United States Patent and Trademark Office*